(12) United States Patent
Lundgren et al.

(10) Patent No.: US 6,451,836 B1
(45) Date of Patent: Sep. 17, 2002

(54) METHOD OF INHIBITING LIVER GLYCOGEN PHOSPHORYLASE WITH 2-ALKYLPYRROLIDINES

(75) Inventors: Karsten Lundgren, Frederiksberg; Palle Jakobsen, Vaerloese; Marit Kristiansen, Soeborg; Leif Nørskov-Lauritsen, Tappernoeje; Lars Naerum, Hellerup, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/138,712

(22) Filed: Aug. 24, 1998

Related U.S. Application Data

(62) Division of application No. 08/892,660, filed on Jul. 14, 1997, now Pat. No. 5,854,272, which is a continuation of application No. PCT/DK96/00373, filed on Sep. 6, 1996.

(30) Foreign Application Priority Data

Sep. 8, 1995 (DK) .............................. 0992/95

(51) Int. Cl.$^7$ ................................ A61K 31/40
(52) U.S. Cl. .................. 514/408; 514/425; 514/866
(58) Field of Search ................. 514/408, 425, 514/866

(56) References Cited

U.S. PATENT DOCUMENTS

| | | | |
|---|---|---|---|
| 3,597,447 A | 8/1971 | Kashihara et al. .......... 548/566 |
| 4,876,268 A | 10/1989 | Koszyk et al. | |
| 4,894,388 A | 1/1990 | Fleet ........................ 514/425 |
| 4,973,602 A | 11/1990 | Koszyk et al. | |
| 5,401,645 A | 3/1995 | Grabner et al. ............. 435/105 |
| 5,695,969 A | 12/1997 | Grabner et al. ............. 435/105 |
| 5,854,272 A | * 12/1998 | Lundgren et al. ........... 514/408 |

FOREIGN PATENT DOCUMENTS

| | | |
|---|---|---|
| EP | 0 322 395 | 12/1987 |
| EP | 0 367 747 | 5/1990 |
| EP | 0 389 723 | 10/1990 |
| EP | 0 403 336 | 12/1990 |
| EP | 0 422 307 | 4/1991 |
| EP | 0 439 444 | 7/1997 |
| JP | 53-46967 | 4/1978 |
| JP | 54-106463 | 8/1979 |
| JP | 61-118360 | 6/1986 |
| JP | 2-212470 | 8/1990 |
| JP | 6-025157 | 2/1994 |
| WO | 9205152 | * 4/1992 |

OTHER PUBLICATIONS

Nash et al., Phytochemistry, vol. 24, No. 7, pp. 1620–1622 (1985).
Furukawa et al., Phytochemistry, vol. 24, No. 3, pp. 593–594 (1985).
Hung et al., J. Org. Chem, vol. 56, pp. 3849–3855 (1991).
Setoi et al., Chem. Pharm. Bull, vol. 35, pp. 3995–3999 (1987).
Fleet et al., Tetrahedron, vol. 42, pp. 5685–5692 (1986).
Fleet et al., Tetrahedron, vol. 44, 2649–2655 (1988).
Fleet et al., Tetrahedron, vol. 26, No. 26, pp. 3127–3130 (1985).
Abstract of JP 61171465 (1986).
Winchester et al., Biochem. J., vol. 290, pp. 743–749 (1993).
Farr et al., Tetrahedron, vol. 50, No. 4, pp. 1033–1044, (1994).
McCaig et al., Tetrahedron, vol. 34, No. 24, pp. 3939–3942 (1993).

* cited by examiner

*Primary Examiner*—Kevin E. Weddington
(74) *Attorney, Agent, or Firm*—Reza Green, Esq.; Cheryl H. Agris, Esq.

(57) ABSTRACT

The present invention relates to (2R,3R,4R)-3,4-dihydroxy-2-hydroxymethylpyrrolidine and other substituted 2-methylpyrrolidines and their use for inhibiting liver glycogen phosphorylase.

24 Claims, No Drawings

METHOD OF INHIBITING LIVER GLYCOGEN PHOSPHORYLASE WITH 2-ALKYLPYRROLIDINES

CROSS-REFERENCE TO RELATED APPLICATIONS

This application is a divisional of U.S. application Ser. No. 08/892,660, filed Jul. 14, 1997 now U.S. Pat. No. 5,854,272 which is a continuation of PCT/DK96/00373 filed Sep. 6, 1996 and claims priority under 35 U.S.C. 119 of Danish application 0992/95 filed Sep. 8, 1995, the contents of which are fully incorporated herein by reference.

FIELD OF THE INVENTION

The present invention relates to the use of 2-alkylpyrrolidines in the treatment of diabetes and pharmaceutical compositions containing these compounds.

BACKGROUND OF THE INVENTION

Diabetes is characterized by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function in association with a range of other abnormalities.

Type 1 diabetic patients are currently treated with insulin. The majority of type 2 diabetic patients are treated either with sulfonylureas that stimulate β-cell function, with α-glucosidase inhibitors which decrease carbohydrate uptake from the intestine in association with meals, or with agents that enhance the tissue sensitivity of the patients towards insulin or with insulin. Among the agents applied to enhance tissue sensitivity towards insulin, metformin is a representative example. Examples of α-glucosidase inhibitors are acarbose and voglibose.

Even though sulfonylureas and α-glucosidase inhibitors are widely used in the treatment of NMDDM, this therapy is, in most instances, not satisfactory: Thus, in a large number of NIDDM patients, sulfonylureas and α-glucosidase inhibitors do not suffice to normalize blood sugar levels and the patients are, therefore, at high risk for acquiring diabetic complications. Also, many patients gradually lose the ability to respond to treatment with sulfonylureas and are gradually forced into insulin treatment. This shift of patients from oral hypoglycaemic agents to insulin therapy is usually ascribed to exhaustion of the β-cells in NIDDM patients.

In normals as well as in diabetics, the liver produces glucose in order to avoid hypoglycemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37 (1988), 667–687; A. Consoli: *Diabetes Care* 15 (1992), 430–441; and J. E. Gerich: *Horm.Metab.Res.* 26 (1992), 18–21). Similarly, if type 1 diabetes is not properly controlled by insulin treatment, hepatic glucose production, particularly from glycogen, will be increased and result in fasting hyperglycemia.

Since existing forms of therapy of diabetes does not lead to sufficient glycaemic control and therefore are unsatisfying, there is a great demand for novel therapeutic approaches. Since the liver in diabetes is known to have an increased glucose production, compounds inhibiting this activity are highly desirable.

Recently, patents on inhibitors of the liver specific enzyme, glucose-6-phosphatase, which is necessary for the release of glucose from the liver, have been filed, for example German Offenlepunisschrift Nos. 4,202,183 and 4,202,184 and Japanese patent application No. 4-58565. All these known compounds are benzene derivatives.

International patent application having publication No. WO 92/16640 relates to di-, tri- and tetrasaccharides that are substrates or inhibitors of glycosyltransferase and glycosidase enzymes. Some specific compounds mentioned therein are 2,3,4,5-tetrahydroxypiperidine, 3,4,5-trihydroxy-6-methylpiperidine and 3,4-dihydroxy-5-methylpiperidine.

International Patent Application No. WO 92/21657 relates to certain ω-deoxyazapyranoses, e.g. 3,4-dihydroxy-5-methyl-piperidine mentioned in claim 16 thereof. It is stated that these compounds have glucosidase inhibiting properties.

European patent application having publication No. 528, 495 A1 relates to a class of azacyclic compounds, i.e. compounds comprising an azacyclic ring system substituted by arylmethyloxy or an arylmethylthio moiety. These compounds may be useful as tachykinin antagonists.

European patent application having publication No. 375, 651 A1 relates to 1,4-dideoxy-1,4-imino-L-allitol and derivatives thereof having glycosidase inhibitory activity.

Moreover, scientifically it is well realized that inhibition of glycogen phosphorylase is a suitable target for the treatment of diabetes (Martin et al., 1991; Biochemistry 30: 10101–16; Oikonomakos et al., 1994; Eur. J. Drug Metab. Pharmakokin. 3: 185–92). These groups have used glucose analogs.

European patent application No. 422,307 relates to preparation of N-glycosyl 1,4-dideoxy-1,4-imino-D-arabinitols as α-glycosidase inhibitors. These compounds are said to be useful in the treatment of diabaetes mellitus.

European patent application No. 389,723 relates to the preparation of iminoarabinitol derivatives as α-glucosidase inhibitors.

U.S. Pat. No. 4,973,602 relates to antiviral (2S,3S,4S) pyrrolidines having benzyloxycarbonyl or an optionally substituted alkylphenyl group in the 1-position. In said US patent, (2S,3S,4S)-1-([4-chlorophenyl]methyl-2-hydroxymethyl-3,4-dihydroxypyrrolidine is specifically mentioned.

European patent application No. 367,747 relates to antiviral (2S,3S,4S) pyrrolidines, e.g. (2S,3S,4S)-2-hydroxymethyl-3,4-dihydroxypyrrolidines having methyl, butyl, hexyl, nonyl, propionyl, 2-hydroxyethyl or 5-hydroxypentyl in the 1-position.

European patent application No. 322.395 describes some pyrrolidines and piperidines, which can be used for the treatment of AIDS. Examples of specific compounds mentioned therein are 2-hydroxymethyl-3,4-dihydroxypyrrolidine and the corresponding 1-methyl derivative.

One object of the present invention is to furnish compounds which can be used as medicaments.

A further object of this invention is to furnish compounds which can effectively be used in the treatment of diabetes.

A still further object of this invention is to furnish compounds which can effectively be used as inhibitors of glucose production from the liver.

A further object of this invention is to furnish compounds which can effectively be used as phosphorylase inhibitors.

BRIEF DESCRIPTION OF THE INVENTION

The present invention relates to compounds of the general formula I stated in the claims below.

Surprisingly, it has been found that the compounds stated in the claims, below, have interesting pharmaco-logical properties. For example, the compounds can be used in the treatment of diabetes. Especially, the compounds are active as inhibitors of glucose production from the liver. Consequently, the compounds can be used for the treatment of the increased plasma glucose levels in diabetics.

DETAILED DESCRIPTION OF THE INVENTION

Hereinafter, the term alkyl, when used alone or in combination with another moiety, is a straight or branched saturated hydrocarbon chain group which preferably contains not more than 8 carbon atoms, more preferred not more than 4 carbon atoms. Especially preferred alkyl groups are methyl, ethyl, propyl and isopropyl.

The term halogen as used herein refers to chloro, bromo or fluoro, preferably fluoro. Preferably, N-alkylamino is N-methylamino. Preferably, N,N-dialkylamino is N,N-dimethylamino. The term acyl as used herein refers to carbonyl sub-stituted with hydrogen, alkyl or phenyl. Herein, cycloalkyl preferably contains 3–7 carbon atoms, more prefered 3–6 carbon atoms. Alkoxy preferably is methoxy or ethoxy. Alkoxycarbonyl preferably is methoxycarbonyl or ethoxycarbonyl. Aralkyl preferably is benzyl. Trifluoroalkyl preferably is trifluoromethyl or 2,2,2-trifluoroethyl. Alkene preferably contains not more than 8 carbon atoms and preferably is allyl. The term "one or more" substituents preferably is 1–3 substituents, most preferred 1.

A subgroup of compounds to be used according to this invention are compounds of formula I wherein the two substituets designated by the symbols $R^3$ and $R^5$ are situated at the same side of the plane formed by the 5 membered nitrogen containing ring, and $R^4$ is situated at the opposite side of the plane formed by the 5 membered nitrogen containing ring. Such compounds are either (2S,3S,4S)-2-alkylpyrrolidines or (2R,3R,4R)-2-alkylpyrrolidines. Among these compounds, the (2R,3R,4R)-2-alkylpyrrolidines are preferred.

Examples of compounds to be used according to this invention are compounds of formula I wherein $R^1$ is alkyl which optionally is substituted with one or more of the following groups: hydroxy, alkoxy, amino, N-alkylamino, N,N-dialkylamino, alkoxycarbonyl, cycloalkyl or optionally substituted phenyl.

Another example of compounds to be used according to this invention are compounds of formula I wherein $R^1$ is phenylalkyl wherein the phenyl moiety optionally is substituted with one or more of the following groups: halogen, hydroxy, alkoxy, trifluoromethyl or cyano.

Another subgroup of compounds to be used according to this invention are compounds of formula I wherein $R^3$ and $R^4$ each are hydroxy, and $R^5$ is hydroxymethyl.

The compounds of formula I may be presented as a mixture of isomers which, if desired, may be resolved into the individual pure enantiomers. This resolution may conveniently be performed by fractional crystallization from various solvents, of the salts of compounds of the formula I with optical active acids or by other methods known per se, for example, chiral column chromatography. This invention includes all isomers, whether resolved or mixtures thereof.

Examples of pharmaceutically acceptable salts are acid addition salts with non-toxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid.

Preferred compounds to be used according to this invention are 3,4-dihydroxy-2-hydroxymethylpyrrolidine, 3,4-dihydroxy-2-hydroxymethyl-1-methylpyrrolidine, 1-cyclopropylmethyl-3,4-dihydroxy-2-hydroxymethylpyrrolidine, 3,4-dihydroxy-2-hydroxymethyl-1-propylpyrrolidine, 1-butyl-3,4-dihydroxy-2-hydroxymethylpyrrolidine,3,4-dihydroxy-2-hydroxymethyl-1-(2,2,2-trifluoroethyl)pyrrolidine, 1-benzyl-3,4-dihydroxy-2-hydroxymethylpyrrolidine, 3,4-dihydroxy-2-hydroxymethyl-1-(2-hydroxyethyl) pyrrolidine, 3,4-dihydroxy-2-hydroxymethyl-1-(1,3-dihydroxyprop-2-yl)pyrrolidine, 3,4-dihydroxy-2-hydroxymethyl-1-(2,3-dihydroxyprop-1-yl)pyrrolidine, 1-(2-aminoethyl)-3,4-dihydroxy-2-hydroxymethylpyrrolidine and salts and hydrates thereof, preferably (2R,3R,4R)-3,4-dihydroxy-2-hydroxymethylpyrrolidine, (2R,3R,4R)-3,4-dihydroxy-2-hydroxymethyl-1-methylpyrrolidine, (2R,3R,4R)-1-cyclopropylmethyl-3,4-dihydroxy-2-hydroxymethylpyrrolidine(2R,3R,4R)-3,4-dihydroxy-2-hydroxymethyl-1-propylpyrrolidine, (2R,3R,4R)-1-butyl-3,4-dihydroxy-2-hydroxymethylpyrrolidine, (2R,3R,4R)-3,4-dihydroxy-2-hydroxymethyl-1-(2,2,2-trifluoroethyl) pyrrolidine, (2R,3R,4R)-1-benzyl-3,4-dihydroxy-2-hydroxymethylpyrrolidine, (2R,3R,4R)-3,4-dihydroxy-2-hydroxymethyl-1-(2-hydroxyethyl)pyrrolidine, (2R,3R,4R)-3,4-hydroxy-2-hydroxymethyl-1-(2,3-hydroxyprop-1-yl) pyrrolidine, (2R,3R,4R)-3,4-dihydroxy-2-hydroxymethyl-1-(1,3-dihydroxyprop-2-yl)pyrrolidine, (2R,3R,4R)-1-(2-aminoethyl)-3,4-dihydroxy-2-hydroxymethylpyrrolidine, (2S,3S,4S)-3,4-dihydroxy-2-hydroxymethylpyrrolidine, (2S,3S,4S)-3,4-dihydroxy-2-hydroxymethyl-1-methylpyrrolidine, (2S,3S,4S)-1-cyclopropylmethyl-3,4-dihydroxy-2-hydroxymethylpyrrolidine,(2S,3S,4S)-3,4-dihydroxy-2-hydroxymethyl-1-propylpyrrolidine, (2S,3S, 4S)-1-butyl-3,4-dihydroxy-2-hydroxymethylpyrrolidine(2S, 3S,4S)-3,4dihydroxy-2-hydroxymethyl-1-(2,2,2-trifluoroethyl)pyrrolidine, (2S,3S,4S)-1-benzyl-3,4-dihydroxy-2-hydroxymethylpyrrolidine, (2S,3S, 4S)-3,4-dihydroxy-2-hydroxymethyl-1-(2-hydroxyethyl)pyrrolidine (2S,3S,4S)-3,4-dihydroxy-2-hydroxymethyl-1-(2,3-dihydroxyprop-1-yl)pyrrolidine, (2S,3S,4S)-3,4-dihydroxy-2-hydroxymethyl-1-(1,3-dihydroxyprop-2-yl)pyrrolidine, (2S,3S,4S)-1-(2-aminoethyl)-3,4-dihydroxy-2-hydroxymethylpyrrolidine and salts and hydrates thereof.

Generally, the compounds of formula I are prepared by methods known per se by the skilled art worker, for example as described in the following. The compounds of formula I can be prepared by joining the C-1 and C-4 of xylose together with nitrogen to form the pyrrolidine ring as described in Tetrahedron 42 (1986), 5685 et seq. A variety of functional groups can be introduced in the compounds prepared as outlined above by methods well known to those skilled in the art.

More specifically, the compounds of formula I can be prepared as follows:

a) Reacting a compound of the general formula II

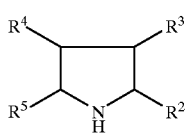

(II)

wherein $R^2$, $R^3$, $R^4$, and $R^5$ are as defined in the claims below, with an aldehyde in presence of a reducing agent among which sodium cyanoborohydride is preferred, to form a compound of formula I.

b) Reacting a compound of the general formula II

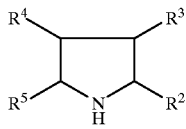

(II)

wherein $R^2$, $R^3$, $R^4$, and $R^5$ are as defined in the claims below, with a compound of the general formula $R^1Y$, wherein $R^1$ is as defined in the claims below, and Y is a leaving group, to form a compound of formula I. The reaction is carried out under alkaline conditions, i.e. in the presence of a base.

The leaving group, Y, may be any suitable leaving group as for example halogen.

c) Reacting a compound of the general formula III

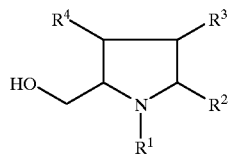

(III)

wherein $R^1$ either is as defined in the claims below or is a readily removable protection group, i.e. benzyl, $R^2$ is as defined in the claims below and $R^3$ and $R^4$ are protected hydroxy, i.e. benzyloxy, with a halogenating agent such as thionyl chloride, thionyl bromide, or diethylaminosulfur trifluoride (DAST) and subsequent removal of the protection groups to form a compound of formula I, wherein $R^1$, $R^3$, and $R^4$ are as defined in the claims below, and $R^5$ is methyl substituted with halogen.

d) Reacting a compound of the general formula IV

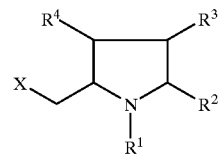

(IV)

wherein $R^1$ either is as defined in the claims below or is a readily removable protection group, i.e. benzyl, $R^2$ is as defined in the claims below, $R^3$ and $R^4$ are protected hydroxy, i.e. benzyloxy, and X is a leaving group, with a compound of the general formula $NHR^6R^7$, wherein the two substituents $R^6$ and $R^7$ may both be alkyl, or one is allyl and the other is hydrogen or together with NH $R^6$ and $R^7$ form phthalimide, and subsequent removal of the protection groups to form the compounds of formula I, wherein $R^1$, $R^2$, $R^3$, and $R^4$ are as defined in the claims below, and $R^5$ is methyl substituted with amino, N-alkylamino, or N,N-dialkylamino.

The leaving group, X, may be any suitable leaving group as for example halogen.

e) Reacting a compound of the general formula I

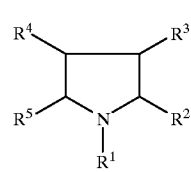

(I)

wherein $R^1$ and $R^2$ are as defined in the claims below, and one or two of the groups $R^3$ and $R^4$ is hydroxy and the remaining is protected hydroxy, i.e. benzyl, $R^1$ is as defined in the claims below or is a corresponding protected group, with a halogenating agent such as thionyl chloride, thionyl bromide or diethylaminosulfur trifluoride (DAST) and subsequent removal of the protection groups to form a compound of the formula I, wherein $R^1$, $R^2$ and $R^5$ are as defined in the claims below, and $R^3$ and $R^4$ are hydroxy or halogen, but not more than one of $R^3$ and $R^4$ is hydroxy.

Pharmaceutical Compositions

This invention further provides pharmaceutical compositions which comprise at least one compound of formula I or a pharmaceutically acceptable salt thereof in connection with a pharmaceutically acceptable carrier. Such compositions may be in the form of powders, solutions, or suspensions, which may or may not be divided in unit dosage form or in the form of capsules or tablets.

The pharmaceutical compositions of this invention may comprise carriers, diluents, absorption enhancers, tablet disintegrating agents and other ingredients which are conventionally used in the art. The powders and tablets preferably contain from 5 to 99%, more preferred from 10 to 90% of the active ingredient. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions suitable for parenteral injection.

The route of administration of the compositions containing a compound of formula I may be any route which effectively transports the active compound to its site of action, the oral or nasal route being preferred.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient. A convenient daily dosage can be less than about 1 g, preferably in the range around 10–200 mg.

The present invention is further illustrated by the following examples which, however, are not to be construed as limiting the scope of protection.

The features disclosed in the foregoing description and in the following examples and claims may, both separately and

EXAMPLE 1

(2R,3R,4R)-3,4-Dibenzyloxy-2-enzyloxymethyl) pyrrolidine (Compound 1)

The title compound was prepared by the method described by Overkleeft et al., Tetrahedron 50 (1994), 4215–4224.

EXAMPLE 2

(2R,3R,4R)-3,4-Dihydroxy-2-(hydroxymethyl) pyrrolidine, hydrochloride (Compound 2)

The title compound was prepared by the method described by Overkleeft et al., Tetrahedron 50 (1994), 4215–4224.

EXAMPLE 3

(2R,3R,4R)-3,4-Dibenzyloxy-2-benzyloxymethyl-1-methylpyrrolidine (Compound 3)

A mixture of (2R,3R,4R)-3,4-dibenzyloxy-2-benzyloxymethylpyrrolidine (Compound 1) (0.5 g, 1.24 mmol), formic acid (10 ml) and 37% formaldehyde (7.5 ml) was heated for 3 hours at reflux temperature and evaporated in vacuo. The residue was dissolved in a mixture of ethyl acetate (25 ml) and 1 N sodium hydroxide (25 ml). The organic phase was isolated, washed once with water, dried over magnesium sulphate and evaporated in vacuo to give (2R,3R,4R)-3,4-dibenzyloxy-2-benzyloxymethyl-1-methylpyrrolidine (0.49 g, yield: 95%) as a golden oil.

$^1$H-NMR (CDCl$_3$) in ppm: δ7.2–7.4 (15H, phenyl), 4.3–4.6 (6H, m, CH$_2$ in benzyl), 3.9 (2H, m, CH$_2$O), 3.5–3.7 (2H, m, 2 CH-O-Bn), 3.15 (1H, d, CHCH$_2$O), 2.4–2.6 (2H, m, CH$_2$N), 2.4 (3H, s, CH$_3$).

$^{13}$C-NMR (CDCl$_3$) in ppm: δ138.4, 138.2, 128.4, 127.9, 127.8, 127.6, 127.5, 86.4, 81.6, 73.3, 71.5, 71.0, 70.9, 70.6, 60.4, 41.7.

EXAMPLE 4

(2R,3R,4R)-3,4-Dihydroxy-2-hydroxymethyl-1-methylpyrrolidine,hydrochloride (Compound 4)

A mixture of (2R,3R,4R)-3,4-dibenzyloxy-2-benzyloxymethyl-1-methylpyrrolidine (Compound 3) (38 mg, 0.067 mmol), 10% Pd/C (30 mg), 4 N HCl (0.1 ml) and 99.9% ethanol (5 ml) was reduced in a Parr apparatus at 40 psi for 20 hours. The mixture was filtered and evaporated in vacuo to give (2R,3R,4R)-3,4-dihydroxy-2-hydroxymethyl-1-methylpyrrolidine, hydrochloride (15 mg, yield 88%) as a yellow oil.

$^{13}$C-NMR (CD$_3$OD) in ppm: δ79.1, 78.1, 75.8, 63.4, 60.7, 44.2

EXAMPLE 5

(2R,3R,4R)-3,4-Dibenzyloxy-2-benzyloxymethyl-1-trifluoro-acetylpyrrolidine (Compound 5)

(2R,3R,4R)-3,4-Dibenzyloxy-2-benzyloxymethylpyrrolidine (Compound 1) (0.5 g, 1.5 mmol) was suspended in ethyl 1,1,1-trifluoroacetate (20 ml). The reaction mixture was heated at reflux temperature for 16 hours. The mixture was cooled and evaporated in vacuo. The residual oil was purified on a silica gel column with diethylether/hexan (1:1) as eluent giving (2R,3R,4R)-3,4-dibenzyloxy-2-benzyloxymethyl-1-trifluoroacetylpyrrolidine (0.5 g, yield: 67%) as an oil.

$^{13}$C-NMR (.CDCl$_3$) in ppm: δ51.4, 63.4, 66.5, 71.4, 71.6, 73.2, 79.8, 81.3, 116 (q), 127.6, 127.7, 127.9, 128.0, 128.4, 128.6, 137.1, 137.4, 138.1, 156(q).

EXAMPLE 6

(2R,3R,4R) 3,4-Dibenzyloxy-2-benzyloxymethyl-1-(2,2,2-trifluoroethyl)pyrrolidine (Compound 6)

(2R,3R,4R)-3,4-Dibenzyloxy-2-benzyloxymethyl-1-trifluoro-acetylpyrrolidine (Compound 5) (0.3 g, 0.6 mmol) was dissolved in tetrahydrofuran (20 ml). The mixture was cooled to 0° C. and 1 M borane-tetrahydrofuran complex (0.6 ml, 6 mmol) added under nitrogen. The reaction mixture was stirred at 0° C. for 2 hours then refluxed for 2 hours. The mixture was cooled and poured into methanol (100 ml). Evaporation in vacuo gave (2R,3R,4R)-3,4-dibenzyloxy-2-benzyloxymethyl-1-(2,2,2-trifluoroethyl)pyrrolidine (0.3 g) as an oil.

$^1$H-NMR (CDCl$_3$) in ppm: δ2.95 (q,1H); 3.15 (m,2H); 3.5 (d,1H); 3.7 (q,3H); 3.9 (m,1H); 4.2 (m,1H); 4.6 (m,6H); 7.45 (s,15H).

$^{13}$C-NMR (CDCl$_3$) in ppm: δ54.9, 55.5, 56.2, 56.8, 58.6, 68.9, 71.2, 71.6, 72.0, 73.4, 81.8, 84.6, 127.7, 127.9, 128.2, 138.1, 138.3.

EXAMPLE 7

(2R,3R,4R)-3,4-Dihydroxy-2-hydroxymethyl-1-(2,2,2-trifluoroethyl)pyrrolidine (Compound 7)

(2R,3R,4R)-3,4-Dibenzyloxy-2-benzyloxymethyl-1-(2,2,2-trifluoroethyl)pyrrolidine (Compound 6) (0.3 g, 0.6 mmol) was dissolved in 96% ethanol (30 ml), and 10% Pd/C (0.1 g) was added under N$_2$. The compound was reduced in a Parr apparatus (40 Psi) for 16 hours. The reaction mixture was filtered and evaporated in vacuo giving (2R,3R,4R)-3,4-dihydroxy-2-hydroxymethyl-1-(2,2,2-trifluoroethyl)pyrrolidine (0.09 g) as an brown oil.

$^1$H-NMR (CDCl$_3$) in ppm: δ3.3 (m, 1H); 3.4 (m,2H); 3.7 (t,d,2H); 3.8 (t broad, 2H); 3.9–4.1 (m,2H); 4.5 (broad s, OH).

EXAMPLE 8

(2R,3R,4R)-3,4-Dibenzyloxy-2-benzyloxymethyl-1-cyclopropyl-methylpyrrolidine, hydrochloride (Compound 8)

(2R,3R,4R)-3,4-Dibenzyloxy-2-benzyloxymethylpyrrolidine (Compound 1) (0.25 g, 0.62 mmol) was dissolved in methyl-isobutylketone (15 ml). Potassium carbonate (0.17 g, 1.2 mmol) and potassium iodide (0.03 g, 0.18 mol) was added. After stirring for 10 min at 25° C. cyclopropylmethylbromide (0.078 ml, 0.81 mmol) was added. The mixture was stirred under a N$_2$ atmosphere at 80° C. for 24 hours and evaporated in vacuo. Water (20 ml) was added and extraction with methylene chloride (3×20 ml), drying of the organic phases with magnesium sulphate and evaporation of the solvent in vacuo afforded a yellow oil. Purification of the crude product twice on a silica gel column (1: Eluent: CH$_2$Cl$_2$/MeOH (19:1) and 2: Eluent: CH$_2$Cl$_2$/MeOH (39:1)) gave (2R,3R,4R)-3,4-dibenzyloxy-2-benzyloxymethyl-1-cyclopropylmethylpyrrolidine (0.213 g, yield: 75%) as an oil.

¹H-NMR (CDCl₃) in ppm: δ7.28 (m, 15H); 4.5 (m, 6H); 3.8 (broad s, 2H); 3.70–3.45 (m, 2H); 3.38 (s) and 3.32 (s) (alltogether 1H); 2.86 (dd, 1H); 2.74 (m, 1H); 2.63 (dd, 1H); 2.11 (dd, 1H); 1.0–0.8 (m,1H); 0.46 (t, 2H); 0.10 (d, 2H).

Conversion of the free base into the hydrochloride salt using 2 M HCl(g) in diethylether gave (2R,3R,4R)-2-benzyloxymethyl-3,4-dibenzyloxy-1-cyclopropylmethylpyrrolidine, hydro-chloride (0.14 g, yield 46%), melting point: 66–67° C.

EXAMPLE 9

(2R,3R,4R)-1-Cyclopropylmethyl-3,4-dihydroxy-2-hydroxymethylpyrrolidine hydrochloride (Compound 9)

To a solution of (2R,3R,4R)-3,4-dibenzyloxy-2-benzyloxy-methyl-1-cyclopropylmethylpyrrolidine, hydrochloride (Compound 8) (0.14 g, 0.28 mmol) in 96% ethanol (15 ml) was added 10% Pd/C (50 mg) and 1 M hydrochloric acid (0.1 ml). The reaction mixture was hydrogenated in Parr apparatus at 40 psi for 24 hours. The mixture was filtered and concentrated in vacuo giving (2R,3R,4R)-1-cyclopropylmethyl-3,4-dihydroxy-2-hydroxymethylpyrrolidine, hydrochloride as a yellow oil (0.063 g, yield: 100%).

¹H-NMR (CD₃OD) in ppm: δ3.96 (broad s, 2H); 3.90 (s,1H); 3.71–3.39 (m, 4H); 3.00 (dd, 1H); 1.24–1.08 (m, 1H); 0.75 (d, 2H); 0.43 (t, 2H).

EXAMPLE 10

(2R,3R,4R)-3,4-Dibenzyloxy-2-benzyloxymethyl-1-butylpyrrolidine (Compound 10).

(2R,3R,4R)-3,4-Dibenzyloxy-2-benzyloxymethylpyrrolidine(Compound 1) (0.7 g, 1.7 mmol) was dissolved in dry methanol. Butyric aldehyde (0.153 ml, 1.7 mmol) and sodium cyanoborohydride (0.107 g, 1.7 mmol) was added. A solution of anhydrous hydrogen chloride in diethylether (2 M) was added dropwise until pH 6. The resulting mixture was stirred for 24 hours at room temperature under a nitrogen atmosphere and evaporated in vacuo. Addition of 1 M sodium hydroxide (50 ml), extraction of the product with diethylether (2×50 ml), drying of the organic phases with magnesium sulphate and evaporation of the solvent in vacuo gave the title compound as a crude oil (0.644 g). Purification of the crude product on a silica gel column (Eluent: methylene chloride/methanol (19:1)) afforded (2R,3R,4R)-3,4-dibenzyloxy-2-benzyloxy-methyl-1-butylpyrrolidine (0.243 g, yield: 30%) as an oil.

¹H-NMR (CDCl₃) in ppm: δ7.28 (m, 15H); 4.51 (m, 4H); 4.45 (2 s, 2H); 3.90 (m, 2H); 3.57 (m, 2H); 3.23 (s) and 3.18 (s) (alltogether 1H); 2.94–2.77 (m, 1H); 2.72 (dd, 1H); 2.55 (dd, 1H); 2.40–2.24 (m, 1H); 1.56–1.18 (m, 4H); 0.90 (t, 3H).

EXAMPLE 11

(2R,3R,4R)-1-Butyl-3,4-dihydroxy-2-hydroxymethylpyrrolidine, hydrochloride (Compound 11)

The title compound was synthesized as described for compound 9 using (2R,3R,4R)-3,4-dibenzyloxy-2-benzyloxymethyl-1-butylpyrrolidine (Compound 10) (0.243 g,0.53 mmol), ethanol (30 ml), 10% Pd/C (0.07 g) and excess of 1 M hydro-chloric acid to convert the amine to the hydrochloride salt. (2R,3R,4R)-1-Butyl-3,4-dihydroxy-2-hydroxymethylpyrrolidine, hydrochloride was obtained as a yellow syrup (0.098 g, yield: 82%).

¹H-NMR (CD₃OD) in ppm: δ4.15 (s, 1H); 3.88 (m, 3H); 3.54 (m, 1H); 3.4 (m, 3H); 3.1 (m, 1H); 1.71 (m, 2H); 1.39 (m, 2H); 0.95 (t, 3H).

EXAMPLE 12

(2R,3R,4R)-1-Acetyl-3,4-dibenzyloxy-2-benzyloxymethylpyrrolidine (Compound 12)

(2R,3R,4R)-3,4-Dibenzyloxy-2-benzyloxymethylpyrrolidine (Compound 1) (0.642 g, 1.6 mmol) was dissolved in dry methylene chloride (15 ml) under a nitrogen atmosphere. Triethylamine (0.288 ml, 2.1 mmol) and acetyl chloride (0.125 ml, 1.8 mmol) were added, and the mixture was stirred for 2 hours at room temperature. Water (20 ml) was added, the layers were separated and the water phase was extracted twice with methylene chloride (2×20 ml).

Drying of the combined organic phases with magnesium sulphate and evaporation of the solvent in vacuo gave the title compound as an crude oil (0.7 g, yield 99%). Purification on silica gel (Eluent: methylene chloride/methanol (19:1)) afforded (2R,3R,4R)-1-acetyl-3,4-dibenzyloxy-2-benzyl-oxymethylpyrrolidine (0.595 g, yield 83%) as an oil.

¹H-NMR (CDCl₃) in ppm: δ7.28 (m, 15H); 4.65–4.33 (m, 7H); 4.12–3.46 (m, 6H); 2.06 (s) and 2.00 (s) (alltogether 3H).

EXAMPLE 13

(2R,3R,4R)-1-Acetyl-3,4-dihydroxy-2-hydroxymethylpyrrolidine (Compound 13)

The title compound was synthesized as described for compound 9 using (2R,3R,4R)-1-acetyl-3,4-dibenzyloxy-2-benzyloxy-methylpyrrolidine (Compound 12) (0.595 g, 1.3 mmol), ethanol (30 ml), methanol (10 ml), 10% Pd/C (0.10 g) and a catalytic amount of 1 M hydrochloric acid. Purification of the product on silica gel (Eluent: Ethyl acetate/methanol (1:1))afford-ed(2R,3R,4R)-1-acetyl-3,4-dihydroxy-2-hydroxymethylpyrrolidine(0.2 g, yield: 86%) as an oil.

¹H-NMR (CD₃OD) in ppm: δ4.10 (broad s, 2H); 3.95–3.70 (m, 4H); 3.51–3.38 (m, 1H); 2.20 (s) and 2.10 (s) (alltogether 3H).

EXAMPLE 14

(2R,3R,4R)-1-Allyl-3,4-dibenzyloxy-2-benzyloxymethylpyrrolidine (Compound 14)

(2R,3R,4R)-3,4-Dibenzyloxy-2-benzyloxymethylpyrrolidine (Compound 1) (1.025 g, 2.5 mmol) was dissolved in methylisobutylketone (15 ml). Triethylamine (0.53 ml, 3.8 mmol) and potassium iodide (0.04 g) were added. The mixture was stirred under a nitrogen atmosphere for 4 hours at 80° C. and 24 hours at room temperature and evaporated in vacuo. Water (40 ml) was added and extraction with methylene chloride (3×40 ml), drying of the organic phases with magnesium sulphate and evaporation of the solvent in vacuo afforded a yellow oil. Purification of the crude product on a silica gel column (Eluent: Heptane/ethyl acetate (9:1)) gave (2R,3R,4R)-1-allyl-3,4-dibenzyloxy-2-benzyloxymethylpyrrolidine (0.91 g, yield: 81%) as an oil.

¹H-NMR (CDCl₃) in ppm: δ7.28 (m, 15H); 6.02–5.82 (m, 1H); 5.25–5.05 (m, 2H); 4.50 (m, 4H); 4.45 (s) and 4.43 (s)

(alltogether 2H); 3.89 (m, 2H); 3.67–3.48 (m, 3H); 3.20 (s) and 3.13 (s) (alltogether 1H); 3.02 (dd, 1H); 2.78 (dd, 1H); 2.60 (dd, 1H).

EXAMPLE 15

(2R,3R,4R)-3,4-Dihydroxy-2-hydroxymethyl-1-propylpyrrolidine (Compound 15)

The title compound was synthesized as described for compound 9 using (2R,3R,4R)-1-allyl-3,4-dibenzyloxy-2-benzyloxymethylpyrrolidine (compound 14) (0.910 g, 2.1 mmol), ethanol (100 ml), 10% Pd/C (0.2 g) and excess of 1 M hydrochloric acid to convert the amine to the hydrochloride salt. After evaporation of the solvent in vacuo the compound was purified on silica gel (Eluent: 2-propanol/ 25% ammonium hydroxide (4:1)) and (2R,3R,4R)-3,4-dihydroxy-2-hydrox-ymethyl-1-propylpyrrolidine was obtained as a yellow crystals (0.279 g, yield: 78%). Melting point: 79–80° C.

$^1$H-NMR (CD$_3$OD) in ppm: δ3.92 (m, 2H); 3.67 (m, 2H); 3.03 (s) and 2.98 (s) (alltogether 1H); 2.87–2.59 (m, 2H); 2.46–2.20 (m, 2H); 1.50 (m, 2H); 0.90 (t, 3H).

EXAMPLE 16

(2R,3R,4R)-1-Benzyl-3,4-dihydroxy-2-hydroxymethylpyrrolidine (Compound 16)

(2R,3R,4R)-2-Hydroxy-3,4-dihydroxymethylpyrrolidine hydrochloride (compound 2) (0.265 g, 1.6 mmol) was dissolved in dry methanol (25 ml), and benzaldehyde (0.159 ml, 1.6 mmol) and sodium cyanoborohydride (0.098 g, 1.6 mmol) was added. A solution of anhydrous hydrogen chloride in diethylether (2 M) was added dropwise until pH 6. The resulting mixture was stirred for 24 hours at room temperature under a nitrogen atmosphere and evaporated in vacuo. Purification of the product on silica gel (Eluent: 2-propanol/methanol (4:1)) afforded (2R,3R,4R)-1-benzyl-3,4-dihydroxy-2-hydroxymethylpyrrolidine (0.304 g, yield: 87%) as an oil.

$^1$H-NMR (CD$_3$OD) in ppm: δ7.40–7.20 (m, 5H); 4.10 (d, J =14Hz, 1H); 3.92 (m, 2H); 3.70 (m, 2H); 3.50 (d, J =14Hz, 1H); 2.90–2.60 (m, 3H).

EXAMPLE 17

(2R,3R,4R)-3,4-Dibenzyloxy-2-benzyloxymethyl-1-(2,3-dihydroxyprop-1-yl)pyrrolidine (Compound 17)

The title compound was synthesized as described for compound 10 using (2R,3R,4R)-3,4-dibenzyloxy-2-benzyloxymethylpyrrolidine (Compound 1) (0.5 g, 1.2 mmol), methanol (30 ml), glyceraldehyde (0.134 g, 1.5 mmol) and sodium cyanoborohydride (0.094 g, 1.5 mmol). Purification of the crude product on silica gel (Eluent: Ethyl acetate) afforded (2R,3R,4R)-3,4-dibenzyloxy-2-benzyloxymethyl-1-(2,3-dihydroxyprop-1-yl)pyrrolidine (0.424 g, yield: 72%) as an oil.

$^1$H-NMR (CDCl$_3$) in ppm: δ7.28 (m, 15H); 4.48 (s, 4H); 4.43 (m, 2H); 3.95 (m, 1H); 3.84 (m, 1H1); 3.78–3.25 (m, 8H); 3.23 (s) and 3.18 (s) (alltogether 1H); 3.02–2.39 (m, 4H).

EXAMPLE 18

(2R,3R,4R)-3,4-Dihydroxy-2-hydroxymethyl-1-(2,3-dihydroxyprop-1-yl)pyrrolidine, hydrochloride (Compound 18)

The title compound was synthesized as described for compound 9 using (2R,3R,4R)-3,4-dibenzyloxy-2-benzyloxymethyl-1-(2,3-dihydroxyprop-1-yl)pyrrolidine (Compound 17) (0.424 g, 0.89 mmol), ethanol (80 ml), 10% Pd/C (0.1 g), and excess of 4 M hydrochloric acid to convert the amine to the hydrochloride salt. (2R,3R,4R)-3,4-Dihydroxy-2-hydroxymethyl-1-(2,3-dihydroxyprop-1-yl) pyrrolidine hydrochloride was obtained as white crystals (0.216 g, yield: 100%) with melting point above 230° C. (decomposition).

$^1$H-NMR (CD$_3$OD) in ppm: δ4.22 (broad s, 1H); 4.0 (m, 4H); 3.8–3.2 (m, 7H).

EXAMPLE 19

(2R,3R,4R)-3,4-Dibenzyloxy-2-benzyloxymethyl-1-(2-phthalimidoethyl)pyrrolidine (Compound 19)

(2R,3R,4R)-3,4-Dibenzyloxy-2-benzyloxymethylpyrrolidine (Compound 1) (0.73 g, 1.8 mmol), N-(2-bromoethyl)phthalimide (0.686 g, 2.7 mmol), triethylamine (0.5 ml, 3.6 mmol) and a catalytic amount of potassium iodide was dissolved in dry dimethylformamide (30 ml). The mixture was stirred for 24 h at 70° C., cooled to room temperature and evaporated in vacuo. Water (60 ml) was added and extraction with methylene chloride (3×60 ml), drying of the organic phases with magnesium sulphate and evaporation of the solvent in vacuo afforded an oil. Purification twice on silica gel (Eluent 1: Heptane/ethyl acetate (1:1) and eluent 2: Petroleum ether/diethylether (2:1)) gave (2R,3R,4R)-3,4-dibenzyloxy-2-benzyloxymethyl-1-(2-phthalimidoethyl)pyrrolidine (0.64 g, yield: 61%) as an oil.

$^1$H-NMR (CDCl$_3$) in ppm: δ7.72 (m, 2H); 7.60 (m, 2H); 7.24 (m, 15H); 4.50 (m, 4H); 4.40 (m, 2H); 4.00–3.64 (m, 4H); 3.53–3.23 (m, 4H); 2.79 (dd, 1H); 2.28 (dd, 1H); 2.7–2.5 (m, 1H).

EXAMPLE 20

(2R,3R,4R)-1-(2-Aminoethyl)-3,4-dibenzyloxy-2-benzyloxymethylpyrrolidine (Compound 20)

(2R,3R,4R)-3,4-Dibenzyloxy-2-benzyloxymethyl-1-(2-phthal-imidoethyl)pyrrolidine (Compound 19) (0.64 g, 1.1 mmol) was dissolved in ethanol (20 ml) and hydrazin, hydrate (0.215 ml, 4.4 mmol) was added. The clear solution was stirred for 4 hours at 40° C. and for 18 hours at room temperature. The white precipitate was filtered off and the filtrate evaporated in vacuo. The residue was partitioned between aqueous hydrochloric acid and methylene chloride. The water phase adjusted to pH 11 with 2 N sodium hydroxide and extracted with methylene chloride (2×100 ml) and with diethylether (100 ml). Drying of the combined organic phases with magnesium sulphate and evaporation of the solvent in vacuo afforded the crude product as an oil. Purification on silica gel (Eluent: Ethyl acetate) gave (2R,3R,4R)-1-(2-aminoethyl)-3,4-dibenzyloxy-2-benzyloxymethylpyrrolidine (0.015 g) as an oil.

$^1$H-NMR (CDCl$_3$) in ppm: δ7.22 (m, 15H); 4.50 (m, 4H); 4.40 (m, 2H); 3.95 (m, 1H); 3.83 (m, 1H); 3.65–3.30 (m, 4H); 3.29 (s) and 3.24 (s) (alltogether 1H); 3.13–2.98 (m, 1H); 2.82 (dd, 1H); 2.67 (dd, 1H); 2.6 (m, 1H).

EXAMPLE 21

(2R,3R,4R)-1-(2-Aminoethyl)-3,4-dihydroxy-2-hydroxymethylpyrrolidine (Compound 21)

The title compound can be synthesized as described for compound 9 using (2R,3R,4R)-1-(2-aminoethyl)-3,4- dibenzyloxy-2-benzyloxymethylpyrrolidine (Compound 20) as starting material.

EXAMPLE 22

(2R,3R,4R)-3,4-Dibenzyloxy-2-benzyloxymethyl-1-(2-hydroxyethyl)pyrrolidine (Compound 22)

The title compound was prepared as described for compound 8 using (2R,3R,4R)-3,4-dibenzyloxy-2-benzyloxymethylpyrrolidine (Compound 1) (0.51 g, 1.27 mmol) and 2-chloroethanol (0.1 ml, 1.49 mmol) as starting material. (2R,3R,4R)-3,4-Dibenzyloxy-2-benzyloxymethyl-1-(2-hydroxyethyl)pyrrolidine was obtained as a golden oil (0.48 g, yield: 85%).

$^1$H-NMR (CDCl$_3$) in ppm: δ7.3 (m, 15H); 4.5 (m, 6H); 4.0 (broad d, 1H); 3.9 (broad d, 1H); 3.6 (m, 4H); 3.25 (d,1H); 3.05 (m, 1H); 2.9 (m, 1H); 2.68 (dd, 1H); 2.6 (dt, 1H).

EXAMPLE 23

(2R,3R,4R)-3,4-Dihydroxy-1-(2-hydroxyethyl)-2-hydroxymethylpyrrolidine, hydrochloride (Compound 23)

The title compound was synthesized as described for compound 9 using (2R,3R,4R)-3,4-dibenzyloxy-2-benzyloxymethyl-1-(2-hydroxyethyl)pyrrolidine (Compound 22) as starting material. (2R,3R,4R)-3,4-Dihydroxy-1-(2-hydroxyethyl)-2-hydroxymethylpyrrolidine, hydrochloride was obtained as an golden oil (0.23 g, yield 100%).

$^1$H-NMR (CD$_3$OD) in ppm: δ4.2 (broad s, 1H), 3.85–4.05 (m, 5H); 3.5–3.8 (m, 4H); 3.25–3.4 (m, 1H)

EXAMPLE 24

Experimental protocol and results

For in vivo studies, female ob/OB mice (20 g) fasted for 3 hours were used. Test compounds or NaCl (0.9%; controls) were administered intraveneously (hereinafter designated i.v.). Glucagon were administered subcutaneously (hereinafter designated s.c.) in order to increase hepatic glucose output derived from glycogen. Blood samples were drawn from the orbital vain and analyzed for glucose using a glucose oxidase method.

Rat hepatocytes were isolated using a standard two step collagenase technique, and cultured onto collagen coated culture dishes for 72 hours in medium 199 with the addition of dexamethazone (0.1 μM); penicillin/Streptomycin ((100 u/100 μg)/ml) and insulin (1 nM). During the last 24 hours, the hepatocytes were cultured in the presence of high levels of insulin (5 nM) and glucose (15 mM), which result in the incorporation of glucose into glycogen. Therefore, at the time of the experiment, the cells mimic livers from fed animals.

Experiments were initiated after 48 hours of culture by 2 times wash of cells and addition of a 20 mM HEPES experimental buffer including balanced salts, but without glucose. The test compound was added simultaneously with the experimental buffer. To some cultures, glucagon (0.5 nM) was added after 10 minutes in order to stimulate glucose production from liver cells. The glucose released into the media, reflecting the glucose production of the liver cells, was measured 70 minutes after the start of the experiment and standardized to cellular DNA content.

Phosphorylase was either purchased from Sigma or extracted from rat livers according to Stalmans et. al. (Eur.J.Biochem. 49 (1974), 415). The activity of phosphorylase was determined as described by Bergmeyer (1983; in: Meth. of Enzymatic Analysis, 2, 293–295, Weinheim, (ed.) Verlag Chemie).

The activity of the glycogen debranching enzyme, α-1, 6-glucosidase, was determined as described by Brown and Brown (1966; in : Meth. in Enzymology, 8, 515–524, Neufeld and Ginsburg (Eds.) Academic Press).

Table 1 below demonstrates the efficacy of (2R,3R,4R)-3,4-dihydroxy-2-hydroxymethylpyrrolidine (Compound 2) in lowering the glucagon mediated increase in plasma glucose. The effects are compared to those in control animals and those in animals treated with 6 fold higher doses of the model α-1,6-glucosidase inhibitor 1-deoxynojirimycin (hereinafter designated dNOJ).

TABLE 1

Effects of (2R,3R,4R)-3,4-dihydroxy-2-hydroxymethylpyrrolidine and the model α-1,6-glucosidase inhibitor on the glucagon mediated increase in blood glucose in mice. Numbers are averages ± S.D.. N = 5.

|  | Delta plasma glucose (mmoles/L) |
| --- | --- |
| Control animals | 6.3 ± 1.0 |
| Compound 2 (8 mg/kg) | 0.5 ± 0.6 |
| dNOJ (50 mg/kg) | 5.7 ± 1.2 |

Table 1 demonstrates that (2R,3R,4R)-3,4-dihydroxy-2-hydroxymethylpyrrolidine (Compound 2) represents a potent principle for reducing blood glucose. In contrast, the α-1,6-glucosidase inhibitor, dNOJ, was unable to reduce blood glucose.

Table 2 below shows the results obtained with (2R,3R,4R)-3,4-dihydroxy-2-hydroxymethylpyrrolidine (Compound 2) on basal and glucagon stimulated glycogenolysis. The effects are compared to those exerted by the α-1,6-glucosidase inhibitor: dNOJ.

TABLE 2

Effects of (2R,3R,4R)-3,4-dihydroxy-2-hydroxymethylpyrrolidine (Compound 2) on baseline and glucagon stimulated glucose production from cultured liver cells. Values are expressed relative to the basal glucose production. Results obtained with the model α-1,6 glucosidase inhibitor, 1-deoxynojirimycin, are shown for comparison.

|  | Glucose production | |
| --- | --- | --- |
|  | Without glucagon | With glucagon (0.5 nM) |
| No addition: | 100% | 233% |
| Compound 2 (1 μM): | 19% | 41% |
| dNOJ (50 μM): | 92% | 195% |

The results clearly demonstrate the ability of (2R,3R,4R)-3,4-dihydroxy-2-hydroxymethylpyrrolidine (Compound 2) to inhibit basal and glucagon stimulated hepatocyte glucose production, while inhibition of α-1,6-glucosidase (dNOJ) was insufficient to suppress hepatic glucose production.

Table 3 compares the potency of various 2-methylpyrrolidines with the potency of dNOJ on various cellular and enzymatic activities.

TABLE 3

Effects of selected pyrrolidines compared to effects of dNOJ on different enzymatic activities. The results are the concentrations of the compounds resulting in half maximal activity (I.C.$_{50}$ μmoles/l).

| Compound | Phosphorlyase | 1,6-glucosidase |
|---|---|---|
| dNOJ | >200 | 1.1 |
| 2 | 0.7 | 0.18[a] |
| 23 | 10 | n.d. |
| 7 | 145 | n.d. |
| 9 | 169 | n.d. |
| 11 | 60 | n.d. | n.d.: not determined
[a]From: Fleet et al. (Tetrahedron 20 (1986), 5685)

It is apparent from the presented data in table 3 that the 2-methylpyrrolidines of this invention are potent inhibitors of liver cell glucose production. Moreover, it is also demonstrated that phosphorylase is inhibited by these compounds in similar low concentrations.

Table 3 also demonstrates that the potent model inhibitor of liver α-1,6-glucosidase was unable to inhibit either liver cell glucose production or phosphorylase.

While α-1,6-glucosidase inhibition is recognized as a principle of reducing blood To glucose in association with a carbohydrate rich meal, the finding that compounds of this invention are able to reduce blood glucose arising from hepatic glucose production, i.e. blood glucose in the fasting state, is new and surprising. The surprising aspect is substantiated by the presented negative results with the model α-1,6-glucosidase inhibitor: dNOJ. These results are in agreement with the results presented by Bollen and Stalmans (Eur.J.Biochem. 181 (1980), 775), who also concluded that α-1,6-glucosidase inhibition is an insufficient principle for inhibition of liver cell glucose production. Furthermore, it was clearly demonstrated by Sels et al. (Netherland J.Med. 44 (1994), 198) that fasting plasma glucose of type 2 diabetic patients was not reduced after treatment with the α-1,6-glucosidase inhibitor, miglitol.

In conclusion, the data demonstrates that the compounds of this invention are able to reduce blood glucose and inhibits glucose production from liver cells. It is also demonstrated that the reduction in blood glucose and liver cell glucose production by the compounds of formula I according to this invention is mediated by inhibition of phosphorylase. Consequently, the compounds of formula I can be used to inhibit both the baseline and glucagon stimulated glucose production from liver cells. Therefore, compounds of formula I will be usefull in the treatment of diabetes.

EXAMPLE 25
Tablets

Tablets which are suitable for oral administration and which contain the below-mentioned components are produced in a manner known per se granulating the active and the auxiliary substances and making them into tablets.

A typical tablet contains 50 mg of the compound of formula I, 100 mg of lactose, 30 mg of corn starch, 3 mg of talc powder, 3 mg of colloidal silicon dioxide and 2 mg of magnesium stearate.

EXAMPLE 26
Capsules

Capsules which are suitable for oral administration contain the below-mentioned components are produced in a manner known per se mixing the active substances with the auxiliary substances and putting them into gelatine capsules.

A typical capsule contains 50 mg of the compound of formula I, 100 mg of lactose, 30 mg of corn starch, 3 mg of talc powder, 3 mg of colloidal silicon dioxide and 2 mg of magnesium stearate.

We claim:

1. A method of inhibiting liver glycogen phosphorylase comprising administering to a subject in need thereof an effective amount of a compound of formula I

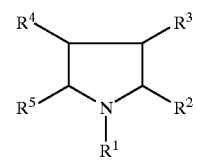

(I)

wherein
   $R^1$ is hydrogen, acyl, alkene, cycloalkyl or alkyl which optionally is substituted with one or more of the following groups: hydroxy, alkoxy, amino, N-alkylamino, N,N-dialkylamino, halogen, cycloalkyl optionally substituted phenyl or alkoxycarbonyl,
   $R^2$ is hydrogen,
   $R^3$ and $R^4$, which are the same or different, independent of each other, is hydrogen, halogen, hydroxy, mercapto or amino which is optionally substituted with alkyl or aralkyl, and
   $R^5$ is alkyl substituted with hydroxy, halogen, amino, N-alkylamino, N,N-dialkylamino or mercapto, or a salt or hydrate thereof.

2. The method according to claim 1, wherein the compound contains at least 2 hydroxy groups.

3. The method according to claim 1, wherein the compound contains at least 3 hydroxy groups.

4. The method according to claim 1, wherein $R^3$ and $R^5$ are situated at the same side of the plane formed by the 5 membered nitrogen containing ring, and $R^4$ is situated at the opposite side of the plane formed by the 5 membered nitrogen containing ring.

5. The method according to claim 1, wherein $R^1$ is hydrogen, acyl or alkyl which is optionally substituted with one or more of the following groups: hydroxy, alkoxy, amino, N-alkylamino, N,N-dialkylamino, phenyl or alkoxycarbonyl.

6. The method according to claim 5, wherein $R^1$ is hydrogen or alkyl.

7. The method according to claim 6, wherein $R^1$ is hydrogen.

8. The method according to claim 1, wherein the optionally substituted phenyl group is phenyl substituted with one or more of the following groups: halogen, hydroxy, alkoxy, trifluoroalkyl or cyano.

9. The method according to claim 1, wherein $R^3$ is hydrogen, hydroxy, halogen or amino.

10. The method according to claim 9, wherein $R^3$ is hydroxy, halogen or amino.

11. The method according to claim 10, wherein $R^3$ is hydroxy or halogen.

12. The method according to claim 11, wherein $R^3$ is hydroxy.

13. The method according to claim 1, wherein $R^5$ is hydrogen, hydroxy, halogen or amino.

14. The method according to claim 13, wherein $R^4$ is hydroxy, halogen or amino.

15. The method according to claim 14, wherein $R^4$ is hydrogen or halogen.

16. The method according to claim 15, wherein $R^4$ is hydroxy or halogen.

17. The method according to claim 16, wherein $R^4$ is hydroxy.

18. The method according to claim 1, wherein $R^5$ is hydroxyalkyl.

19. The method according to claim 18, wherein $R^5$ is hydroxymethyl, hydroxyethyl or hydroxypropyl.

20. The method according to claim 19, wherein $R^5$ is hydroxymethyl.

21. The method according to claim 1, wherein $R^5$ is hydroxymethyl or benzyloxymethyl.

22. The method according to claim 1, wherein the compound is 3,4-dihydroxy-2-hydroxymethylpyrrolidine, 3,4-dihydroxy-2-hydroxymethyl-1-methylpyrrolidine, 1-cyclopropylmethyl-3,4-dihydroxy-2-hydroxymethylpyrrolidine, 3,4-dihydroxy-2-hydroxymethyl-1-propylpyrrolidine, 1-butyl-3,4-dihydroxy-2-hydroxymethylpyrrolidine, 3,4-dihydroxy-2-hydroxymethyl-1-(2,2,2-trifluoroethyl)pyrrolidine, 1-benzyl-3,4-dihydroxy-2-hydroxymethylpyrrolidine, 3,4-dihydroxy-2-hydroxymethyl-1-(2-hydroxyethyl)pyrrolidine, 3,4-dihydroxy-2-hydroxymethyl-1-(1,3-dihydroxyprop-2-yl)pyrrolidine, 3,4-dihydroxy-2-hydroxymethyl-1-(2,3-dihydroxyprop-1-yl)pyrrolidine, 1-(2-aminoethyl)-3,4-dihydroxy-2-hydroxymethylpyrrolidine, 3,4-dihydroxy-2-hydroxymethylpyrrolidine or a salt or optical isomer thereof.

23. The method according to claim 22, wherein the compound is (2R,3R,4R)-3,4-dihydroxy-2-hydroxymethylpyrrolidine, (2R,3R,4R)-3,4-dihydroxy-2-hydroxymethyl-1-methylpyrrolidine, (2R,3R,4R)-1-cyclopropylmethyl-3,4-dihydroxy-2-hydroxymethylpyrrolidine(2R,3R,4R)-3,4-dihydroxy-2-hydroxymethyl-1-propylpyrrolidine, (2R,3R,4R)-1-butyl-3,4-dihydroxy-2-hydroxymethylpyrrolidine, (2R,3R,4R)-3,4-dihydroxy-2-hydroxymethyl-1-(2,2,2-trifluoroethyl)pyrrolidine, (2R,3R,4R)-1-benzyl-3,4-dihydroxy-2-hydroxymethylpyrrolidine, (2R,3R,4R)-3,4-dihydroxy-2-hydroxymethyl-1-(2-hydroxyethyl)pyrrolidine, (2R,3R,4R)-3,4-dihydroxy-2-hydroxymethyl-1-(2,3-dihydroxyprop-1-yl)pyrrolidine, (2R,3R,4R)-3,4-dihydroxy-2-hydroxymethyl-1-(1,3-dihydroxy-prop-2-yl)pyrrolidine, (2R,3R,4R)-1-(2-aminoethyl)-3,4-dihydroxy-2-hydroxymethylpyrrolidine, (2S,3S,4S)-3,4-dihydroxy-2-hydroxymethylpyrrolidine, (2S,3S,4S)-3,4-dihydroxy-2-hydroxymethyl-1-methylpyrrolidine, (2S,3S,4S)-1-cyclopropylmethyl-3,4-dihydroxy-2-hydroxymethylpyrrolidine, (2S,3S,4S)-3,4-dihydroxy-2-hydroxymethyl-1-propylpyrrolidine, (2S,3S,4S)-1-butyl-3,4-dihydroxy-2-hydroxymethylpyrrolidine, (2S,3S,4S)-3,4-dihydroxy-2-hydroxymethyl-1-(2,2,2-trifluoroethyl)pyrrolidine, (2S,3S,4S)-1-benzyl-3,4-dihydroxy-2-hydroxymethylpyrrolidine, (2S,3S,4S)-3,4-dihydroxy-2-hydroxymethyl-1-(2-hydroxyethyl)pyrrolidine, (2S,3S,4S)-3,4-dihydroxy-2-hydroxymethyl-1-(2,3-dihydroxy-prop-1-yl)pyrrolidine, (2S,3S,4S)-3,4-dihydroxy-2-hydroxymethyl-1-(1,3-dihydroxyprop-2-yl)pyrrolidine, (2S,3S,4S)-1-(2-aminoethyl)-3,4-dihydroxy-2-hydroxymethylpyrrolidine, or (2R,3R,4R)-3,4-dihydroxy-2-hydroxymethylpyrrolidine.

24. A method of inhibiting liver glycogen phosphorylase comprising administering to a subject in need thereof an effective amount of (2R,3R,4R)-3,4-dihydroxy-2-hydroxymethylpyrrolidine.

\* \* \* \* \*

UNITED STATES PATENT AND TRADEMARK OFFICE
CERTIFICATE OF CORRECTION

PATENT NO.    : 6,451,836 B1
DATED         : September 17, 2002
INVENTOR(S)   : Lundgren et al.

It is certified that error appears in the above-identified patent and that said Letters Patent is hereby corrected as shown below:

<u>Column 16,</u>
Line 62, "wherein $R^5$" should read -- wherein $R^4$ --

Signed and Sealed this

Ninth Day of March, 2004

JON W. DUDAS
*Acting Director of the United States Patent and Trademark Office*